(12) United States Patent
Russell et al.

(10) Patent No.: US 7,563,818 B2
(45) Date of Patent: Jul. 21, 2009

(54) PHOTOSENSITIZER FUNCTIONALISED NANOPARTICLES

(75) Inventors: David Andrew Russell, Norfolk (GB); Duncan Christopher Hone, Norfolk (GB)

(73) Assignee: Cancer Research Technology Limited, London (GB)

( * ) Notice: Subject to any disclaimer, the term of this patent is extended or adjusted under 35 U.S.C. 154(b) by 551 days.

(21) Appl. No.: 10/494,331

(22) PCT Filed: Oct. 31, 2002

(86) PCT No.: PCT/GB02/04935

§ 371 (c)(1),
(2), (4) Date: Nov. 15, 2004

(87) PCT Pub. No.: WO03/037297

PCT Pub. Date: May 8, 2003

(65) Prior Publication Data

US 2005/0058713 A1    Mar. 17, 2005

(30) Foreign Application Priority Data

Nov. 1, 2001   (GB) ................................. 0126236.9

(51) Int. Cl.
*A61K 31/28*    (2006.01)
*A61K 31/282*   (2006.01)
*A61K 31/295*   (2006.01)
*A61K 31/30*    (2006.01)
*A61K 31/315*   (2006.01)
*A61K 8/02*     (2006.01)
*A61K 8/19*     (2006.01)
*A61K 8/27*     (2006.01)
*A61K 9/00*     (2006.01)
*A61K 9/14*     (2006.01)

(52) U.S. Cl. ....................... 514/492; 514/495; 514/499; 514/501; 514/502; 424/400; 424/489; 977/773; 977/904; 977/911

(58) Field of Classification Search ................. 424/489, 424/490, 618, 630, 646, 649
See application file for complete search history.

(56) References Cited

U.S. PATENT DOCUMENTS 5,178,986 A * 1/1993 Zampini et al. ............. 430/190

FOREIGN PATENT DOCUMENTS

| WO | WO97/10811 |   | 3/1997 |
| WO | WO 97/10811 | * | 3/1997 |
| WO | WO99/61911 |   | 12/1999 |
| WO | WO 99/61911 | * | 12/1999 |
| WO | WO01/08660 |   | 2/2001 |

OTHER PUBLICATIONS

Chambrier et al, Synthesis, Oct. 1995, pp. 1283-1286, Synthesis and Characterisation of Functionalised Phthalocyanine . . . .
Hone et al, Langmuir, 18, 2002, pp. 2985-2987, Generation of Cytotoxic Singlet Oxygen via Phthalocyanine-Stabilized Gold . . . .
Brust et al, J Chem Soc Chem Commun, 1994, pp. 801-802, Synthesis of Thiol-derivatised Gold Nanoparticles in a . . . .
Terrill et al, J Am Chem Soc, 1995, 117, pp. 12537-12548, Monolayers in Three Dimensions: NMR, SAXS, Thermal, and . . . .
Templeton et al, J Am Chem Soc, 1998, 120, pp. 4845-4849, Gateway Reactions to Diverse, Polyfunctional Monolayer . . . .
Chen et al, Langmuir, 15, Oct. 29, 1998, pp. 682-689, Arenethiolate Monolayer-Protected Gold Clusters.
Aguila et al, Langmuir 2000, 16, pp. 5949-5954, Monolayer-Protected Clusters with Fluorescent Dansyl Ligands.
Chen et al, Langmuir 2000, 16, pp. 3543-3548, Monolayer-Protected Cluster Growth Dynamics.
Templeton et al, ACC Chem Res 2000, 33, pp. 27-36, Monolayer-Protected Cluster Molecules.
Hostetler et al, Colloid and Interface Sci, 1997, 2, pp. 42-50, Colloids and self-assembled monolayers.
Badia et al, J Am Chem Soc 1997, 119, pp. 2682-2694, Structure and Dynamics in Alkanethiolate Monolayers Self-Assembled on . . . .
Brust et al, J Chem Soc Chem Commun 1995, pp. 1655-1656, Synthesis and Reactions of Functionalised Gold Nanoparticles.
Buining et al, Langmuir 1997, 13, pp. 3921-3926, Preparation of Functional Silane-Stablized Gold Colloids in the . . . .
Hostetler et al, J Am Chem Soc 1996, 118, pp. 4212-4213, Monolayers in Three Dimensions: Synthesis and Electrochemistry . . . .
Peter Gregory, High Tech Applns of Organic Colorants, 1991, pp. 59-212, Chapter 7, Electrophotography.
Snow et al, Phthalocyanines Prop and Applns., 1989, pp. 345-392 Chapter 5, Phthalocyanine Films in Chemical Sensors.
Wöhrle et al, Adv Mater 3, 1991, pp. 129-138, Organic Solar Cells.
Bonnett, Chem Soc Revs, 1995, pp. 19-33, Photosensitizers of the Porphyrin and Phthalocyanine Series for Photodynamic . . . .

(Continued)

*Primary Examiner*—Johann R Richter
*Assistant Examiner*—James H Alstrum Acevedo
(74) *Attorney, Agent, or Firm*—Jacobson Holman PLLC

(57) ABSTRACT

The present invention relates to self-assembly of a photosensitizer on a nanoparticle. The invention also provides methods for production of functionalized (eg. stabilized) nanoparticles. The nanoparticles may be used in Photodynamic Therapy (PDT). The invention can provide, for example, self-assembled phthalocyanine monolayers (SAMs), wherein the monolayer is formed on a metallic nanoparticle. The term "metallic" as used herein refers to metals, metal oxides and other metal-containing compositions.

According to the invention a functionalized nanoparticle comprises:
 a metallic core;
 a photosensitizer monolayer chemically bonded to said core, said monolayer containing molecules capable of photo-excitation to produce a reactive oxygen species such as singlet oxygen, from oxygen molecules; and
 a phase transfer reagent.

26 Claims, 6 Drawing Sheets

OTHER PUBLICATIONS

Cook et al, Photochem and Photobiol, vol. 62, No. 3, 1995, pp. 542-545, Octa-Alkyl Zinc Phthalocyanines: Potential . . . .

Ometto et al, Brit Jour of Cancer 1996, 74, pp. 1891-1899, Tumour-localising and -photosensitising properties of a novel . . . .

Fabris et al, Jour of Photochem and Photobiol 39, 1997, pp. 279-284, Tumour-localizing and tumour-photosensitizing . . . .

Weishaupt et al, Cancer Res 36, Jul. 1976, pp. 2326-2329, Identification of Singlet Oxygen as the Cytotoxic Agent in . . . .

Simpson et al, Langmuir, vol. 13, No. 3, pp. 460-464, Evanescent Wave Excited Fluorescence from Self-Assembled Phthalocyanine . . . , 1996.

Revell et al, Jour of Mater Chem, 2000, 10, pp. 31-37, Formation and spectroscopic characterisation of self-assembled . . . .

Imahori et al, J Am Chem Soc 2001, 123, pp. 335-336, Photo-active Three-Dimensional Monolayers: Porphyrin-Alkanethiolate . . . .

Schmidt et al, J Phys Chem 98, 2874, 1994, pp. 37-49, Time-Resolved Singlet Oxygen Detection.

Wilkinson et al, J Phys Chem Ref Data, vol. 22, No. 1, 1993, Quantam Yields for the Photosensitized Formation of the . . . .

Darwent et al, J Chem Soc Faraday Trans 2, 1982, 78, pp. 347-357, Excited Singlet and Triplet State Electron-transfer . . . .

Fink et al, Chem Mater 1998, 10, pp. 922-926, Self-Organization of Nanosized Gold Particles.

Chen et al, Langmuir 2001, 17, pp. 733-739, Reversible Transference of Au Nanoparticles across the Water and Toluene . . . .

Simpson et al, Analyst, Oct. 1996, vol. 121, pp. 1501-1505, Surface Plasmon Resonance of Self-assembled Phthalocyanine . . . .

Simpson et al, Sensors and Actuators B29, 1995, pp. 353-357, Formation and characterisation of a self-assembled . . . .

\* cited by examiner

Figure 1. 1, 4, 8, 11, 15, 18 - hexahexyl-22-(11-mercaptoundecyl)-25-methyl phthalocyanine. (Compound I.)

PHOTOSENSITIZER FUNCTIONALISED NANOPARTICLES

This is a nationalization of PCT/GB02/04935 filed Oct. 31, 2002 and published in English.

The present invention relates to self-assembly of a photosensitiser on a nanoparticle. The invention also provides methods for production of functionalised (eg. stabilised) nanoparticles. The nanoparticles may be used in Photodynamic Therapy (PDT). The invention can provide, for example, self-assembled phthalocyanine monolayers (SAMs), wherein the monolayer is formed on a metallic nanoparticle. The term "metallic" as used herein refers to metals, metal oxides and other metal-containing compositions.

BACKGROUND

The synthesis of gold nanoparticles has been shown to take place via the reduction of $HAuCl_4$ in the presence of alkanethiols.[1-5] Recently, there have been an increasing number of reports on the preparation and utilization of such thiol-stabilised gold nanoparticles; often referred to as monolayer-protected clusters (MPC).[6] Potential applications of these types of systems include optical devices, microelectronics, catalysis and chemical recognition.[7-9] In this regard, a great deal of attention is now focused on the functionalisation of the stabilising ligands.[10-12]

Phthalocyanines (Pcs) have been shown to have potential applications in the areas of electrophotography[13], chemical sensors[14], photovoltaic cells[15] and as second generation photosensitisers in the anti-cancer modality termed photodynamic therapy (PDT).[16,17]

Other photosensitiser materials are known as such. For example, porphyrins can act as a photosensitiser.

Of the many prospective uses of photosensitisers such as phthalocyanines or porphyrins, we are interested in the potential of these macrocyclic compounds in the field of PDT.[18,19] PDT involves the selective bio-distribution of a suitably designed photosensitiser molecule near to or within a cell to be killed. Once located, the photosensitiser is excited using light. Excited state energy is then transferred from the triplet state of the sensitiser to the ground state of molecular oxygen producing the cytotoxic species singlet oxygen ($^1O_2$).[20] The generation of the latter species is the principal target for the present invention.

Cancerous cells are just one possible application for this technology. The formation of singlet oxygen will initiate the destruction of a multitude of disease inducing or diseased cells, or indeed bacteria or viruses. The mode of cell kill is due to the highly oxidising nature of singlet oxygen. A photosensitiser can be defined as "a molecule which when excited by light (usually visible although possibly ultraviolet or near infrared) produces a reactive oxygen species, either singlet oxygen or an oxygen free radical, which is cytotoxic".

Previously we have reported the self-assembly of Pc molecules on 2D planar gold films, with attachment of the macrocyclic ring via a mercaptoalkyl tether.[21]

SUMMARY OF THE INVENTION

The present invention provides the first successful preparation of photosensitiser functionalised (eg. stabilised) metallic nanoparticles (3D assemblies). The preferred embodiment uses a substituted zinc phthalocyanine attached to a gold nanoparticle with a C11 mercaptoalkyl tether[22] in association with a phase transfer reagent. These nanoparticles can generate singlet oxygen with high quantum yields which is due, in part, to an association of the phase transfer reagent used in their synthesis.

FIGURES

DETAILED DESCRIPTION OF THE PREFERRED EMBODIMENT OF THE INVENTION

Figure 1:
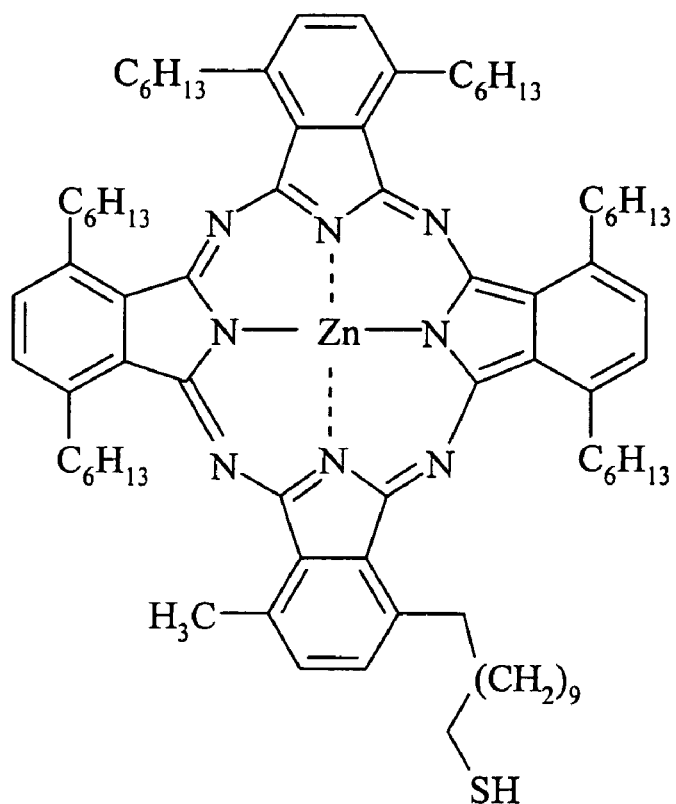
FIG. 1 shows "Compound I", which is 1, 4, 8, 11, 15, 18-hexahexyl-22-(11-mercaptoundecyl)-25-methyl phthalocyanine.

The synthesis of the gold nanoparticles was carried out based on the method of Brust et al.[1] Briefly, $HAuCl_4$ was dissolved in water (30.0 ml; 30 mM) to give a clear yellow solution. Tetraoctylammonium bromide (TOAB) transfer reagent was dissolved in toluene (80 ml; 50 mM). On mixing the two solutions $AuCl_4^-$ is transferred from the aqueous phase to the toluene to give a dark red solution. After stirring for 30 mins the aqueous phase becomes colourless at which point it is removed. Phthalocyanine Compound I (0.84 mmols) was added to the toluene solution (to give a Au:S of 1:0.93) and stirred for a further 20 mins. A freshly prepared aqueous solution of $NaBH_4$ (25 ml; 0.4 M) was rapidly added to the toluene phase and vigorously stirred for a further 3 hrs. Separation of free and bound phthalocyanine was achieved using a silica tlc plate and a solvent system of toluene: methanol (95:5). It should be noted that the free Pc may be recycled using this synthetic approach.

Gold particles, without addition of the Pc, were also prepared. These particles were stable in the original toluene solution but could not be successfully precipitated and redispersed. In the absence of the stabilising thiolated-Pc ligand, large clusters of gold particles of the order of 100 nm diameter were formed as observed by Transmission Electron Microscopy (TEM) and the surface plasmon band in the UV/Visible absorption spectrum.

Figure 2:
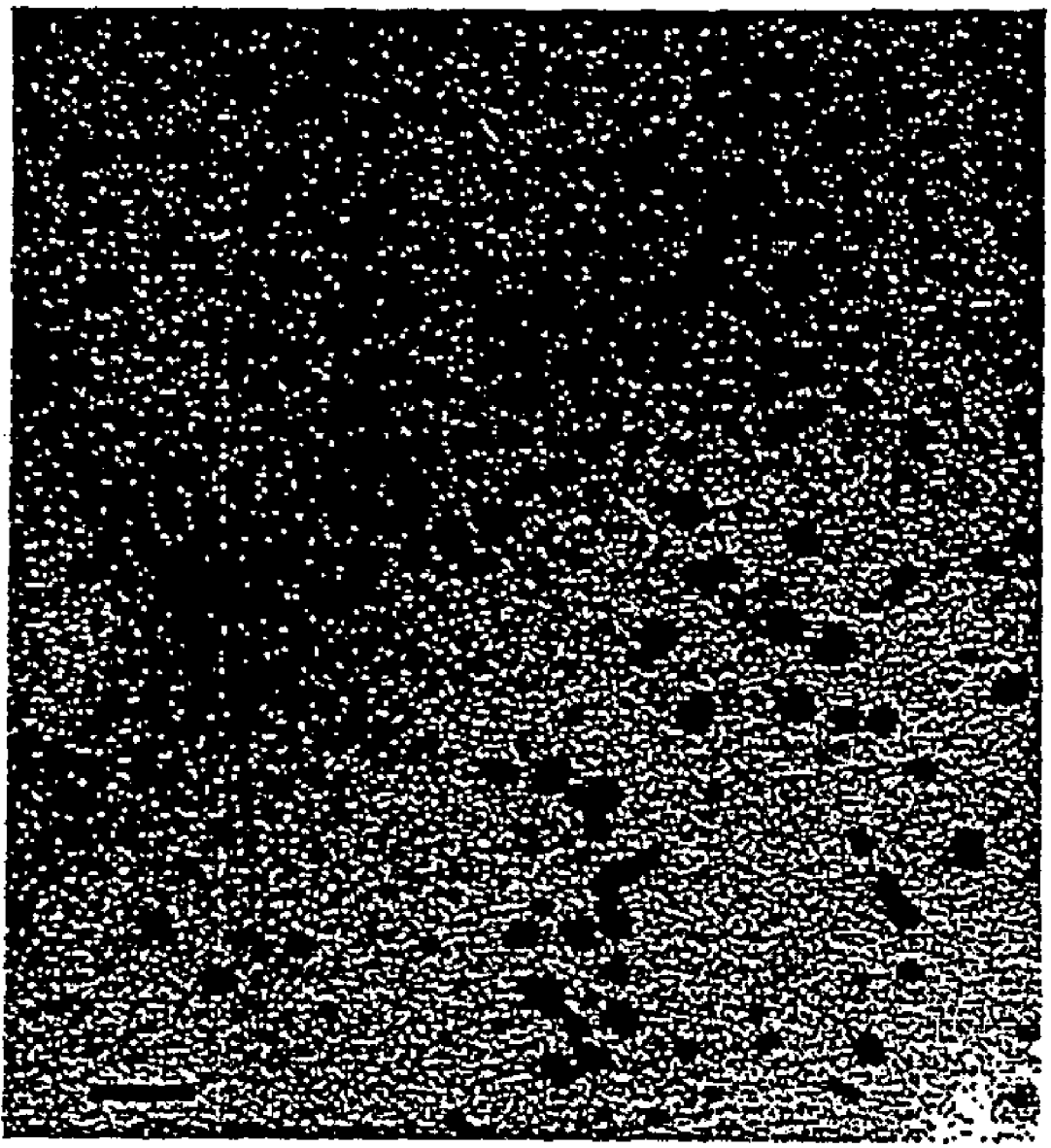
FIG. 2 shows a transmission electromicrograph of Pc-stabilised gold nanoparticles (2-4 nm). The scale bar represents 20 nm.

Transmission electron micrographs of the Pc-gold nanoparticles are consistent with those reported by several groups for other thiol-stabilized MPCs in that they show small, 2-4 nm, non-aggregated particles—FIG. 2. The 2-4 nm diameter particles shown in FIG. 2 suggests that the Pc molecule is acting as a stabilising monolayer. Once separated from the unbound Pc it was observed that the Pc-coated nanoparticles became soluble in a range of polar solvents (e.g. ethanol, methanol, DMSO) in which the unbound form is insoluble. A similar change in solubility was recently reported by Imahori et al.[23] for a porphyrin self-assembled on gold nanoparticles used as an artificial photosynthetic material.

Figure 3:
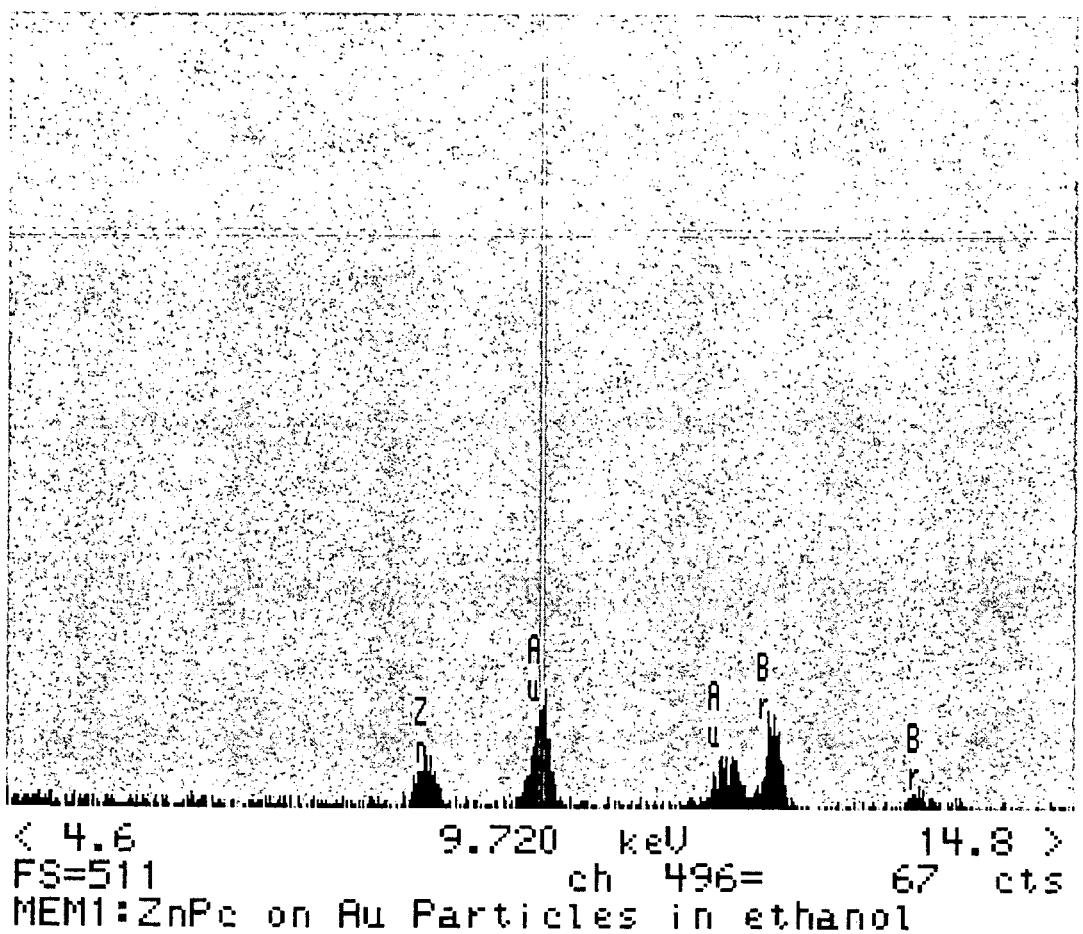
FIG. 3 shows an EDXA spectrum of phthalocyanine stabilised gold nanoparticles showing the presence of gold ($L\alpha$ 9.71 keV, $L\beta$ 11.44 keV), zinc ($L\alpha$ 8.63 keV) and bromine ($K\alpha$ 11.90 keV, $K\beta$ 13.38 keV).

Energy dispersive X-ray analysis (EDXA, FIG. 3) of the Pc-coated nanoparticles not only confirmed the presence of the Pc macrocycle, with a Zn(II) signal ($L\alpha$ 8.63 keV), but also indicated the presence of bromine ($K\alpha$ 11.90; $K\beta$ 13.38 keV) suggesting that the TOAB phase transfer reagent was associated with the gold nanoparticles.

Such a 3 component system (gold nanoparticle/photosensitiser/phase transfer reagent) would be particularly advantageous as the transfer reagent enables the solubilisation of bound hydrophobic macrocycles in polar solvents permitting the systemic delivery of such sensitisers in PDT.

Figure 4:
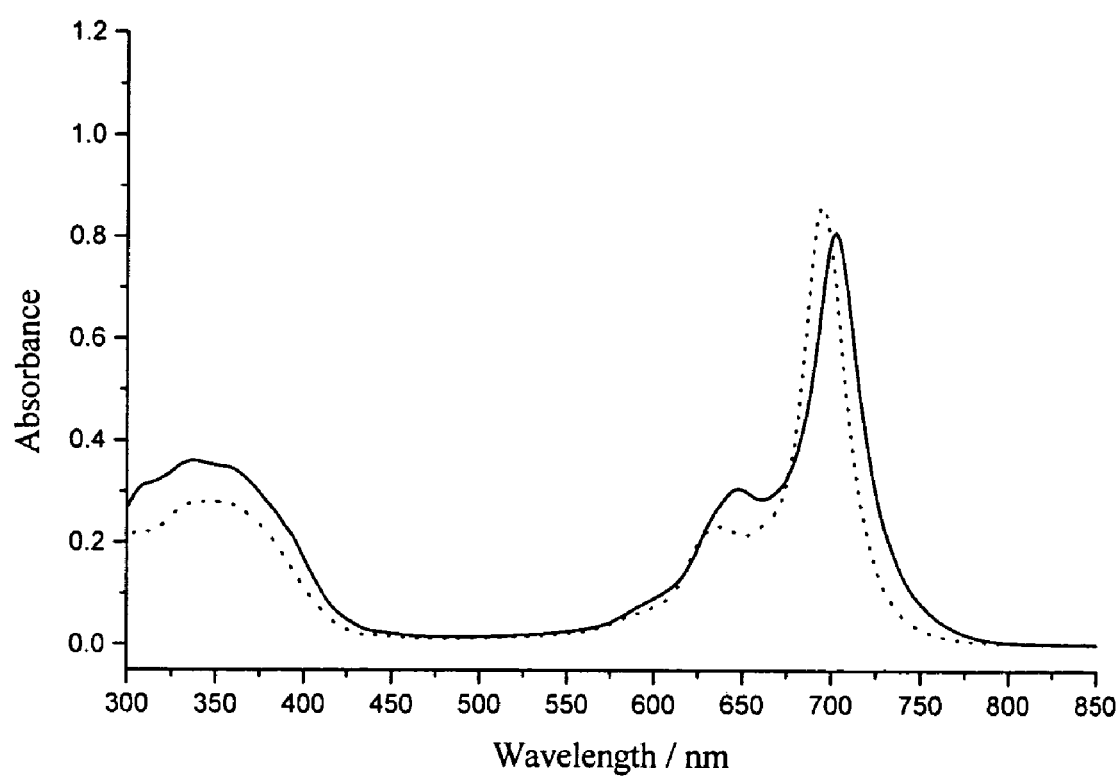
FIG. 4 shows the UV/Visible absorption spectra of free (-) and bound (---) zinc phthalocyanine.
Figure 5A:
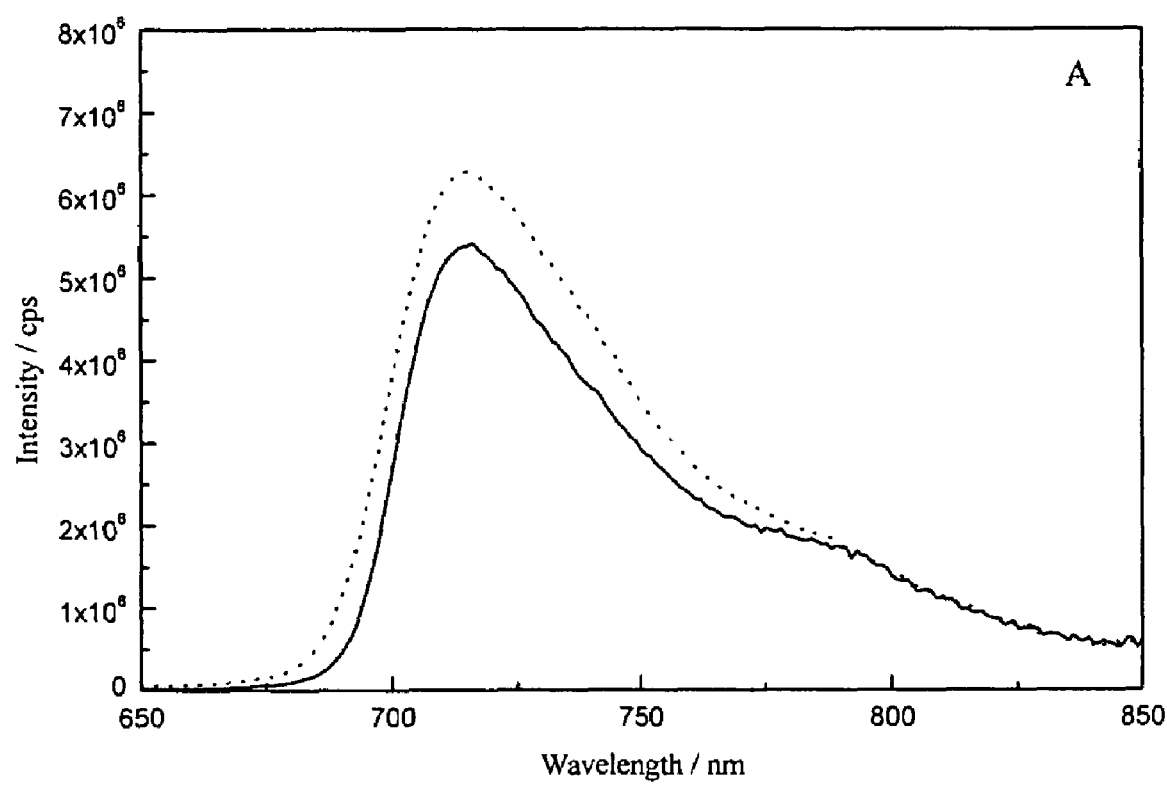
FIG. 5 shows the Fluorescence emission spectra of free (-) and bound (---) zinc phthalocyanine excited at (A) 350 nm and (B) 640 nm.
Figure 5B:
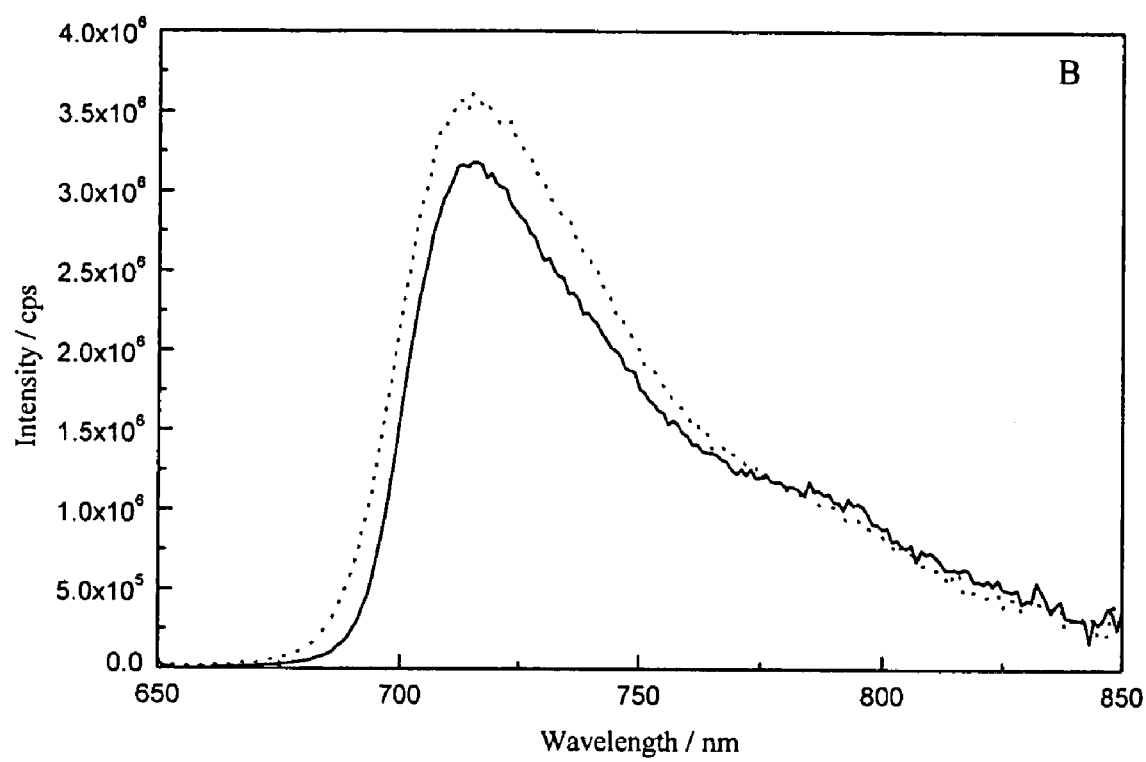

The visible absorption spectrum (FIG. 4) of the Pc coated gold nanoparticles (in methanol) shows a Q band $\lambda_{MAX}$ at 695 nm. This value is blue shifted by 7 nm as compared to the free Pc in toluene, although the difference is possibly due to the differing solvents. However, a photosensitizer with a $\lambda_{MAX}$ of 695 nm would be ideal for PDT with consideration of the depth of skin penetration of radiation at this wavelength.[16] Additionally, fluorescence steady state and lifetime information have been obtained for both the free and bound Pc. Fluorescence emission data have been obtained previously from 2D Pc assemblies where the mercaptoalkyl tether is ideally $C_{11}$, or longer, to prevent quenching by the metal surface.[21] No evidence of quenching of fluorescence ($\lambda_{em}$=715 nm) from the Pc-coated nanoparticles was observed possibly due to a combination of the $C_{11}$ alkyl tether employed and the small gold core (FIG. 5).

Fluorescence lifetime ($\tau$) measurements were obtained by using the method of time-correlated single photon counting. For both the free and bound phthalocyanine optimum fits ($X_2$) were obtained for the double exponential and $\tau_1$ and $\tau_2$ values are shown in table 1.

TABLE 1

The photochemical properties of the free and bound Pc.

| Sample | $\tau_1$/ns (yield) | $\tau_2$/ns (yield) | $\phi_\Delta$ |
|---|---|---|---|
| Free Pc (in toluene) | 2.1 (91%) | 1.11 (9%) | 0.45 |
| Pc-nanoparticles (in ethanol) | 1.8 (98%) | 3.6 (2%) | 0.65 |

It is apparent that the self-assembly of the Pc macrocycle to the gold nanoparticles decreases the principal fluorescence lifetime as compared to the free molecule. This suggests that energy transfer from the excited singlet state of the Pc macrocycle to the metal surface does occur. A decrease in the fluorescence lifetime of the bound Pc is consistent with the data obtained for porphyrin coated gold nanoparticles.[23] Although in both instances any associated TOAB may contribute to the reduced lifetime. Addition of 1 mM TOAB to the free Pc in toluene decreased the value of $\tau_1$ to 0.7 ns (76%) [$\tau_2$=1.7 ns (24%)]. This result suggests that the phase transfer reagent has a direct effect on the singlet state lifetime of the free Pc which is also (partially) observed when the Pc is bound to the gold nanoparticles.

Singlet oxygen quantum yields, $\Phi_\Delta$, for both the free and bound Pc were determined (Table 1) using the method of Nonell and Braslavsky.[24] The Pc coated nanoparticles were referenced to perinapthenone in ethanol ($\Phi_\Delta$=0.97)[25], whilst free Pc was referenced to perinapthenone and octa-decyl zinc phthalocyanine[17] in toluene ($\Phi_\Delta$=1.0 and 0.7 respectively). After deoxygenation of the Pc samples no singlet oxygen could be detected. Furthermore, excitation of a solution of dodecanethiol-stabilised gold nanoparticles was found not to produce singlet oxygen. The value of $\Phi_\Delta$ of 0.45 for the free Pc in toluene is consistent with previous measurements of similar metallated Pcs.[26]

With the addition of 1 mM TOAB to the free Pc an increase in $\Phi_\Delta$ of ca. 10% was observed. Surprisingly, with the 3 component Pc coated gold nanoparticles, $\Phi_\Delta$ increases by ca. 50% to a value of 0.65. It is apparent that the association of the TOAB phase transfer reagent not only affects the excited singlet state of the free and bound Pc but also the triplet energy transfer to molecular oxygen to form the excited singlet oxygen species. With the free Pc molecule we observed that addition of TOAB reduces aggregation of the Pc molecule as evidenced by a sharpening of the Q-absorption band in the UV-visible spectrum (data not shown). It is thought that the geometry of the gold nanoparticles, and possibly the associated TOAB, prevents the macrocycles aggregating on the metal surface and the consequent quenching of the triplet excited state.

It is apparent that the 3 component metal nanoparticles can generate singlet oxygen with enhanced quantum yields as compared to free photosensitiser. The association of the transfer reagent also promotes the solubility of the surface bound hydrophobic sensitiser in polar solvents which would facilitate their systemic injection. The 3 component structures of this invention can provide a useful vehicle for the delivery of photodynamic agents in PDT by virtue of the cytotoxic efficacy of these photosensitiser coated nanoparticles.

It is to be expected that the thiol moiety of the phthalocyanine derivative would initiate the spontaneous formation of a monolayer on either a planar (2D) or nanoparticle gold surface. We have shown previously that the intensity of a fluorescence signal from the bound phthalocyanine monolayer (on the planer surface) is dependent on the chain length of the alkyl tether. Singlet oxygen measurements have not been reported in the literature on molecules self-assembled on planar surfaces.

On transferring the monolayer technology from 2D to 3D systems there are two possibilities with regard to the intensity of fluorescence and the ability to generate singlet oxygen of the phthalocyanine on the gold nanoparticles, i.e. the metal surface could interact with the phthalocyanine causing a quenching of the fluorescence or the opposite effect could have been observed. The same question regarding singlet oxygen levels could be posed but of course there are no data for planar surfaces.

In order to facilitate the formation of a phthalocyanine monolayer bound to the gold nanoparticle a phase transfer reagent is required as per the method of Brust et al. We had assumed that the TOAB phase transfer reagent should be removed using chromatography procedures. When we removed the TOAB, singlet oxygen yields for the phthalocyanine bound nanoparticles were much lower than the free phthalocyanine in solution. However, if you do not fully separate the TOAB from the bound phthalocyanine, i.e. the TOAB is still associated with the coated metal particles, as per the procedure above, then not only does the solubility of the phthalocyanine gold particles change enabling the use of human compatible solvents but the singlet oxygen yields are significantly enhanced by about 50%. While an enhancement in the singlet oxygen yield is observed when TOAB is added to the free phthaloyanine in solution, by about 10%, the significantly enhanced levels obtained with our 3 component (eg. Pc/TOAB/gold nanoparticle) system would not be expected.

Description of Alternative Embodiments of the Invention

Whilst the invention has been described above with regard to the presently preferred embodiments, the scope is not limited thereto. Alternatives exist for the various elements of the 3D assemblies of this invention as described below. These alternatives may be employed singly or in combination with other variants:

1. Metallic Nanoparticle

Nanoparticles are solid, generally spheroid, particles. The nanoparticles we have made are formally cuboctahedron in shape but can be other shapes. The shape can include many possibilities, i.e., truncated octahedra, cuboctahedra, rods and spheres. As used herein the term refers to particles with a size of 500 or 300 or 250 or 100 nm or less, preferably between 1 and 5, more preferably between 2 and 4 nm.

"Nanoparticles for use in Photodynamic Therapy" have previously been described, but these were larger particles in the size range 10-1000 nm and were made from polymeric material, not metallic (ref: WO 97/10811 Novartis).

A number of metallic materials may be used as the core of the nanoparticle. Our preferred material is a metal, preferably gold. The metal may be selected alternatively from other metals such as, for example but not limited to: silver, copper, platinum, palladium, nickel, iron. The invention does not exclude the possible use of metallic materials such as metal oxides as the core. Two examples of such cores would be made from $Fe_2O_3$ or $Fe_3O_4$. A core comprising or consisting of an iron oxide may have a diameter between 3 and 60 nm, for example about 15 nm.

2. Photosensitiser

As used in the present invention the essential feature of a photosensitiser material is that it should be capable of deposition on a suitable metallic nanoparticle core as a "self-assembled monolayer" (SAM), and that it should be capable of acting as a photosensitiser molecule in the field of PDT.

The currently preferred photosensitiser is a Phthalocyanine (Pc) or Pc derivative.

It is known from solution studies that zinc complexed in a Pc can significantly enhance singlet oxygen quantum yield as compared to the yield from metal-free Pc. Hence we currently prefer to include zinc in the centre of the Pc macrocyclic ring. However, inclusion of other enhancers (eg. other metals or non-metals such as silicon) as Pc complexes, and the use of metal-free Pc compounds is not intended to be excluded from the scope of the present invention.

3. Tether

The mercaptoalkyl tether, by which the Pc binds to the derivatised surface of the nanoparticle core, is an important feature of the preferred embodiment of the invention. An alkyl chain length of C11 is currently preferred, and this is consistent with the results of previous published work carried out on the chain length dependency of fluorescence signals from C11, C8 and C3 tethered Pc compounds assembled as SAMs on planar (2D) gold surfaces (ref: (21)).

However, use of other suitable chain lengths for the tether is not intended to be excluded from the scope of the present invention. In particular the term "mercapto-alkyl tether" as used herein is intended to cover moieties which have alkyl chains of any length and which can tether a Pc macrocycle to a metal nanoparticle via the thiol moiety. The preferred chain length is currently considered to be between C8 and C14, eg C11.

The photosensitiser can be attached by other means to the nanoparticle surface rather than just via a mercaptoalkyl (—SH) tether. For example a (—S—S—) disulfide linkage could be used. We have previously published the synthesis[22] and the formation[29] of a metal free diphthalocyanine disulfide [two phthalocyanine molecules attached via a disulfide linkage] to a 2D planar gold surface for optical sensing applications. It will be appreciated that the core nanoparticle should be functionalised in such a way that it can react to allow self-assembly of the photosensitiser molecular layer. Hence, the photosensitiser may encompass molecules which contain moieties other than thiols and disulphides, provided these can self-assemble on the metallic core nanoparticle.

4. Phase Transfer Reagents

The present invention requires an element of the 3 component final-product nanoparticle to be a phase transfer reagent. One class of suitable reagents are quaternary ammonium compounds, of which a preferred reagent is TOAB. Other reagents may be suitable for the same purpose.

Quaternary ammonium compounds (cationic detergents) are synthetic derivatives of ammonium chloride. The general structure is of the form,

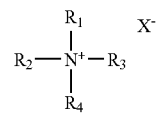

where $R_{1-4}$ represents alkyl or aryl substituents (tetrahedrally arranged) and X represents a halogen, such as bromide or chloride.

This class of compound possesses a variety of chemical and physical properties due to the large number of substituents which may be changed. For example, $R_{1-4}$ may all be long alkyl chains (e.g. $(C_8H_{17})_4NBr$—tetraoctylammonium bromide) or $R_{1-3}$ may be methyl groups with $R_4$ being a long alkyl chain (e.g. $C_{16}H_{33}N(CH_3)_3Br$—cetyltrimethylammonium bromide). As such they can be found in a variety of commercial products, including disinfectants, shampoo and hair conditioners, bitumen/asphalt, antiseptics, fabric conditioners and as microbiocides in water treatment. Notably they are also common in many medicinal preparations and benzalkonium chloride is widely used as a preservative in nasal spray formulations and ophthalmic solutions. See Table 2.

The surfactant like properties of these compounds means that they can locate at the interface between water and oil phases—a property exploited in the technique of phase transfer catalysis. Quaternary ammonium salts provide a means of transfer (or extraction) of a reactant in one phase into another phase which ordinarily it would not be soluble (e.g. from water to oil) and therefore facilitate reactions between chemical species located in different phases. For quaternary ammonium salts this occurs via ion-pair formation between the cation ($N^+$) and the anion of the reactant species. The choice of transfer reagent is strongly dependent upon the hydrophobicity of the molecule. For transfer of reagent anions from water to oil the transfer reagent must not be soluble in water, but be able to form the cation ($N^+$) at the interface. Additionally the choice of alkyl groups ($R_{1-4}$) is important, as this will significantly effect the self-assembly process of the transfer reagent. In this respect the choice of long alkyl chains of equal length, as is the case with tetraoctylammonium bromide disfavours aggregation.

For quaternary ammonium salts where only one or two of the R groups are long alkyl chains (the others being $CH_3$), the formation of aggregates in either the oil (reversed micelles) or water (micelles) may well result in a less efficient-transfer process.

The preparation of gold nanoparticles using a two-phase liquid-liquid system was first reported by Brust et al.[1]. Water-soluble $HAuCl_4$ is transferred from an aqueous phase to an oil phase (typically toluene) via ion-pair formation with a quaternary ammonium salt, tetraoctylammonium bromide (TOAB). The reaction proceeds at the interface between the oil and water phases where the halide anion is dissociated from the ammonium ion.

A 4:1 excess of the transfer reagent over Au and vigorous stirring of the reaction mixture in order to increase the interfacial area both promote transfer to the oil.

The tetraalkylammonium bromide, $R_4N^+Br^-$, class of compound has also been used by Fink et al.[27] to successfully prepare Au nanoparticles with R representing a straight chain alkyl group of differing length ($C_6$, $C_8$ (TOAB), $C_{10}$, $C_{12}$, $C_{16}$ and $C_{18}$) None of these compounds are soluble in water and thus prove to be good transfer reagents. However, for shorter alkyl chain lengths the molecule becomes less and less hydrophobic and will be soluble in the water phase, i.e., not transfer the Au ion as shown by Chen et al.[28] in a study of the transference of gold particles across a water: toluene interface.

TABLE 2

Some example of Quaternary ammonium compounds and their uses.

| Name | Formula | Typical Use |
|---|---|---|
| Cetyltrimethyammonium bromide | $C_{16}H_{33}N(CH_3)_3Br$ | Detergents |
| Benzalkonium Chloride | $C_xH_{25}N(CH_3)_2C_7H_7Cl$ X = typically 12-14 | Preservative in eye drop formulations |
| Cetalkonium Chloride | $C_{16}H_{33}N(CH_3)_2C_7H_7Cl$ | Antiseptics/Disinfectants |
| Tetraoctylammonium bromide | $(C_8H_{17})_4NBr$ | Transfer Reagent |
| Tetrahexylammonium chloride | $(C_6H_{13})_4NCl$ | Transfer Reagent |
| Distearyldimethylammonium chloride | $(C_{18}H_{37})_2N(CH_3)_2Cl$ | Fabric Conditioners |

The use of any suitable phase transfer reagent is contemplated as falling within the scope of the invention.

REFERENCES (1) Brust, M.; Walker, M.; Bethell, D.; Schiffrin, D, J.; Whyman, R. *J. Chem. Soc. Chem. Comm.*, 1994, 801-802
(2) Terrill, R. H.; Postlethwaite, T. A.; Chen, C. H.; Poon, C. D.; Terzis, A.; Chen, A. D.; Hutchison, J. E.; Clark, M. R.; Wignall, G.; Londono, J. D.; Superfine, R.; Falvo, M.; Johnson, C. S.; Samulski, E. T.; Murray, R. W. *J. Am. Chem. Soc.*, 1995, 117, 12537-12548.
(3) Templeton, A. C.; Hostetler, M. J.; Warmoth, E. K.; Chen, S. W.; Hartshorn, C. M.; Krishnamurthy, V. M.; Forbes, M. D. E.; Murray, R. W. *J. Am. Chem. Soc.*, 1998, 120, 4845-4849.
(4) Chen, S. W.; Murray, R. W. *Langmuir*, 1999, 15, 682-689.
(5) Aguila, A.; Murray, R. W. *Langmuir*, 2000, 16, 5949-5954.
(6) Chen, S. W.; Templeton, A. C.; Murray, R. W. *Langmuir*, 2000, 16, 3543-3548.
(7) Templeton, A. C.; Wuelfing, M. P.; Murray, R. W. *Acc. Chem. Res.*, 2000, 33, 27-36.
(8) Hostetler, M. J.; Murray, R. W. *Curr. Opin. Colloid and Interface Sci.*, 1997, 2, 42-50.
(9) Badia, A.; Cuccia, L.; Demers, L.; Morin, F.; Lennox, R. B. *J. Am. Chem. Soc.*, 1997, 119, 2682-2692.
(10) Brust, M.; Fink, J.; Bethell, D.; Schiffrin, D. J.; Kiely, C. *J. Chem. Soc. Chem. Comm.*, 1995, 1655-1656.
(11) Buining, P. A.; Humbel, B. M.; Philipse, A. P.; Verkleij, A. J. *Langmuir*, 1997, 13, 3921-3926.
(12) Hostetler, M. J.; Green, S. J.; Stokes, J. J.; Murray, R. W. *J. Am. Chem. Soc.*, 1996, 118, 4212-4213.
(13) Gregory, P. *High Technology Applications of Organic Colorants*, Plenum Press, New York, 1991.
(14) Snow, A. W.; Barger, W. R. In *Phthalocyanines Properties and Applications*, ed. Leznoff. C. C.; Lever, A. B. P. VCH Publishers, New York, 1989, p. 341.
(15) Wöhrle, D.; Meissener, D. *Advanced Materials*, 1991, 3, 129.
(16) Bonnett, R. *Chem. Soc. Rev.*, 1995, 24, 19-33.
(17) Cook, M. J.; Chambrier, I.; Cracknell, S. J.; Mayes, D. A.; Russell, D. A. *Photochem. Photobiol.*, 1995, 62, 542-545.
(18) Ometto, C.; Fabris, C.; Milanesi, C.; Jori, G.; Cook, M. J.; Russell, D. A. *Br. J. Cancer*, 1996, 74, 1891-1899;
(19) Fabris, C.; Ometto, C.; Milanesi, C.; Jori, G.; Cook, M. J.; Russell, D. A. *J. Photochem. Photobiol. B-Biol.*, 1997, 39, 279-284
(20) Weishaupt, K. R.; Gomer, C. J.; Dougherty, T. J. *Cancer Research*, 1976, 36, 2326-2329.
(21) Simpson, T. R. E.; Revell, D. J.; Cook, M. J.; Russell, D. A. *Langmuir*, 1997, 13, 460-464; Revell, D. J.; Chambrier, I.; Cook, M. J.; Russell, D. A. *J. Mater. Chem.*, 2000, 10, 31-37.
(22) Chambrier, I.; Cook, M. J.; Russell, D. A. *Synthesis-Stuttgart*, 1995, 1283-1286.
(23) Imahori, H.; Arimura, M.; Hanada, T.; Nishimura, Y.; Yamazaki, I.; Sakata, Y.; Fukuzumi, S. *J. Am. Chem. Soc.*, 2001, 123, 335-336.
(24) Nonell, S.; Braslavsky, S. L. In *Singlet Oxygen, UV-A and Ozone, Methods in Enzymology*, Vol. 319, ed. Packer, L.; Sies, H. Academic Press 2000, p 37.
(25) Wilkinson, F.; Helman, W. P.; Ross, A. B. *J. Phys. Chem. reference data*, 1993, 22, 113-262.
(26) Darwent, J. R.; McCubbin, I.; Phillips, D. *J. Chem. Soc.—Faraday Trans. II*, 1982, 78, 347-357.
(27) J. Fink, C. J. Kiely, D. Bethell, D. J. Schiffrin. *Chemistry of Materials* 10 (1998) 922.
(28) S. H. Chen, H. Yao, K. Kimura. *Langmuir* 19 (2001) 733.
(29) T. R. E. Simpson, M. J. Cook, M. C. Petty, S. C. Thorpe and D. A. Russell, Analyst, 1996, 121, 1501-1505; T. R. E Simpson, D. A Russell, I. Chambrier, M. J. Cook, A. B Horn and S. C. Thorpe, Sensors and Actuators B: Chemical, 1995, 29, 353-357.

The invention claimed is:

1. A functionalised nanoparticle, which is a 3D assembly, comprising:
   a metallic core;
   a photosensitiser monolayer chemically bonded to said core, said monolayer containing molecules capable of photo-excitation to produce singlet oxygen, from oxygen molecules; and
   a phase transfer reagent;
   wherein the phase transfer reagent is a cationic detergent; and
   wherein the photosensitiser is phthalocyanine.

2. The nanoparticle according to claim 1, wherein the core comprises or consists of metal(s) selected from gold, silver, copper, platinum, palladium, nickel, iron.

3. The nanoparticle according to claim 2, wherein the core is gold.

4. The nanoparticle according to claim 1, wherein the photosensitiser is a zinc complexed phthalocyanine.

5. The nanoparticle according to claim 1, wherein the phase transfer reagent is a quaternary ammonium compound.

6. The nanoparticle according to claim 5, wherein the phase transfer reagent is TOAB.

7. The nanoparticle according to claim 5, wherein the transfer reagent is a halide salt of the quaternary ammonium compound.

8. The nanoparticle according to claim 5, wherein the transfer reagent is a hydrophobic molecule having four straight chain alkyl groups, said alkyl groups having chain lengths each being selected from the group consisting of $C_6$, $C_8$, $C_{10}$, $C_{12}$, $C_{16}$ and $C_{18}$.

9. The nanoparticle according to claim 7, wherein the transfer reagent is insoluble in water.

10. The nanoparticle according to claim 1, wherein the monolayer is formed by self-assembly during the formation of the core.

11. The nanoparticle according to claim 1, wherein the core has a size of 500, 300, 250, 100 nm or less.

12. The nanoparticle according to claim 11, wherein the core has a size of between 1 nm and 5 nm.

13. The nanoparticle according to claim 12, wherein the core has a size of between 2 nm and 4 nm.

14. The nanoparticle according to claim 1 wherein the core comprises gold and has a diameter between 1 and 5 nm.

15. The nanoparticle according to claim 14, wherein the core has a diameter between 2 nm and 4 nm.

16. The nanoparticle according to claim 1 wherein the core comprises iron oxide and has a diameter between 3 and 60 nm.

17. The nanoparticle according to claim 16, wherein the core has a diameter of about 15 nm.

18. The nanoparticle according to claim 1, wherein the photosensitiser is linked to the core by a mercaptoalkyl tether moiety.

19. The nanoparticle according to claim 18 wherein the mercaptoalkyl tether has an alkyl carbon chain length of C8 to C14.

20. The nanoparticle according to claim 19 wherein the mercaptoalkyl tether has an alkyl carbon chain length of C11.

21. A pharmaceutical composition comprising; nanoparticles according to claim 1; and a pharmaceutically acceptable excipient or carrier; for use as a photosensitiser in photodynamic therapy.

22. A method for producing a nanoparticle according to claim 3 which includes the steps of:
dissolving $HAuCl_4$ in water;
adding phase transfer reagent in solution in an organic solvent;
allowing transfer of $AuCl_4^-$ from the aqueous phase to the organic phase;
separating and retaining the organic phase;
adding mercaptoalkyl-functionalised phthalocyanine to the organic phase;
adding reducing agent; and
separating and collecting phthalocyanine-stabilised gold nanoparticles having associated therewith phase transfer reagent.

23. A method for producing singlet oxygen, from oxygen molecules, which comprises the steps of:
providing a photosensitiser moiety which comprises or consists of a nanoparticle according to claim 1; and exciting the photosensitiser with light in the presence of molecular oxygen.

24. The method according to claim 23, wherein the method is carried out in vitro.

25. The method according to claim 23, wherein the method is carried out in vivo on nanoparticles contained within or located on or beside cancerous cells.

26. A method of treatment of cancerous cells with cytotoxic singlet oxygen, which method comprises administering to the cancerous cells nanoparticles according to claim 1, or a pharmaceutical composition comprising nanoparticles according to claim 1 and a pharmaceutically acceptable excipient or carrier for use as a photosensitiser in photodynamic therapy; and exciting the nanoparticles with red light in the presence of molecular oxygen.

* * * * *